United States Patent [19]

Ledden et al.

[11] Patent Number: 4,810,635
[45] Date of Patent: Mar. 7, 1989

[54] SPECIFIC BINDING ASSAYS EMPLOYING LABEL ANALOG TO REDUCE SAMPLE INTERFERENCES

[75] Inventors: David J. Ledden; Dwight E. Schroedter, both of Elkhart, Ind.

[73] Assignee: Miles Inc., Elkhart, Ind.

[21] Appl. No.: 852,418

[22] Filed: Apr. 16, 1986

[51] Int. Cl.⁴ .................. G01N 33/53; C07H 19/00; C07H 17/00; C07H 21/00

[52] U.S. Cl. ........................ 435/7; 436/825; 536/22; 536/24; 435/810

[58] Field of Search ............... 435/7; 436/825

[56] References Cited

U.S. PATENT DOCUMENTS

| | | | |
|---|---|---|---|
| 4,238,565 | 12/1980 | Hornby et al. | 435/7 |
| 4,318,983 | 2/1982 | Hornby et al. | 435/7 |
| 4,582,791 | 4/1986 | Khanna et al. | 436/825 |
| 4,666,831 | 5/1987 | Janoff et al. | 436/825 |

*Primary Examiner*—Esther M. Kepplinger
*Assistant Examiner*—Janelle Graeter
*Attorney, Agent, or Firm*—Andrew L. Klawitter

[57] ABSTRACT

A specific binding assay, e.g., immunoassay, method and reagent system wherein a structural analog of the label portion of the labeled reagent is included in the reaction mixture to interact with potentially interfering substances in the test sample. The label analog is selected or designed to be substantially inactive in the assay detection system. The invention improves the precision of the assays, particularly homogeneous immunoassays, by significantly reducing or eliminating the variable interaction, e.g., binding, of the labeled reagent by interfering substances in the test sample.

12 Claims, 1 Drawing Sheet

SPECIFIC BINDING ASSAYS EMPLOYING LABEL ANALOG TO REDUCE SAMPLE INTERFERENCES

BACKGROUND OF THE INVENTION

Specific binding assays enable the detection of a particular analyte in a test sample based on the specific binding interaction between the analyte and an appropriate binding partner. The binding between the analyte and its binding partner is most often measured by use of a labeled reagent which becomes bound to the analyte, the binding partner, or some other intermediary binding substance as a function of the presence or amount of analyte in the test sample. Examples are where analyte is detected by binding of a labeled form of the binding partner or where analyte competes with a labeled form of the analyte itself or an analog thereof for binding to a binding partner. A common binding interaction between the analyte and binding partner is the immunochemical binding of an antigen or hapten to a corresponding antibody, although other binding phenomena such as hormone/receptor, drug/receptor, and like interactions as well as nucleic acid hybridization can be employed Assays of this type are well known to be susceptible to a wide range of interferences potentially affecting any one of a number of performance parameters such as precision, sensitivity, specificity, and the like. Oftentimes the interferences are due to substances present in the test sample which cannot be controlled. Minimizing sample interference effects can be particularly vexing since the causative agent may not be evident nor easily determinable. Presented with a specific binding assay exhibiting an unacceptable sample interference, the skilled worker in many cases has no assurance that the interference can be significantly reduced, much less eliminated, by any predetermined modification of the assay procedure or reagent ingredients.

A number of approaches are known for attempting to reduce or minimize sample interferences in specific binding assays. For example, in order to eliminate non-specific label (analyte-fluorescein) binding to endogeneous serum proteins in the fluorescence polarization immunoassay (FPIA) for digoxin, serum samples are treated with trichloroacetic acid (TCA) to remove all serum proteins prior to analysis. Similarly, endogenous serum fluorescence [which has been shown to interfere with the detection of digoxin by the fluorescence energy transfer immunoassay (FETI)] can be eliminated by pretreatment of the sample with a strong oxidizing agent. Clearly, interferences are not unique to homogeneous immunoassays but have also been observed in heterogeneous assay systems. For example, nonspecific binding of enzyme labeled antibodies to polystyrene tubes or plates in enzyme linked immunosorbent assays (ELISAs). This type of interference has been eliminated by the use of detergents and/or proteins (e.g., bovine serum albumin) in the pretreatment of ELISA plates or tubes or by inclusion of these substances in the enzyme antibody label buffer.

In many specific binding assays, the amount of labeled reagent present in the assay mixture must be known or fixed in order for precise measurement of the analyte to be accomplished. The labeled reagent, as is known, comprises a label portion, which provides the detectable response by which the analyte is determined, and a specific binding portion which participates in the various binding interactions upon which the principle of the assay is based. Where the amount of labeled reagent in the reaction mixture is critical, the presence of substances in the test sample which will effectively alter the availability of the labeled reagent either to produce its detectable response or participate in the necessary binding interactions, can substantially affect the precision of the assay performance. This can be particularly acute where the analyte is present in relatively low concentrations in the test sample and assay performance must be quite sensitive.

Reduction of non-specific binding of a fluorescer-labeled antibody to a slide in immunofluorescence tissue staining methods by addition of a structural analog having no fluorescence or low level fluorescence of a different wavelength is disclosed in European Patent Application No. 140,602. The presence of FAD-binding proteins in human blood is disclosed by Farhangi and Osserman, New Engl. J. Med. 294:177–183(1976) and Merrill et al, Recent Findings Concerning Mammalian Riboflavin-Binding Proteins, in *Flavins and Flavoproteins*, Massey and Williams ed., Elsevier/North Holland (New York 1982) pp. 508–513. Armeta et al, Anal. Biochem. 146:211–219(1985) describe the use of inactive β-galactosidase to adsorb and inactivate a serum inhibitory factor in an enzyme immunoassay using β-galactosidase as the label.

The present invention is intended to provide means for controlling sample interferences in specific binding assays which interferences are suspected or found by investigation to be due to the presence of substances in the sample that interact with the label portion of the labeled reagent.

SUMMARY OF THE INVENTION

It has now been found that the performance of specific binding assays can be markedly improved where the sample contains a potentially interfering substance which interacts with the label portion of the labeled reagent by including in the assay mixture a structural analog of the label portion. Thus, the label analog rather than the label portion of the labeled reagent becomes the principal component with which the interfering substance from the sample interacts, thus effectively blocking the interference effect on the labeled reagent. The invention particularly applies to those assays wherein it is known or suspected that a substance or substances in the test sample may interact with the label portion of the labeled reagent to effectively reduce its ability to be detected or to affect the ability of the binding portion of the labeled reagent to participate in its binding interactions.

The invention applies generally to any specific binding assay for determining an analyte in a test sample suspected to contain such a potentially interfering substance. In such assays, the test sample is combined with a reagent system that includes the labeled reagent. The labeled reagent comprises the label and specific binding portions, with the label portion providing a predetermined detectable response. The combination of sample and reagents results in the formation of a bound-species and a free-species of the labeled reagent in the reaction mixture where the proportion of labeled reagent in such respective species is a function of the presence or amount of analyte present in the test sample. The detectable response of the label portion is thereafter measured in the bound- and/or free-species, depending on the particular heterogeneous or homogeneous format followed, and is related to the amount of analyte in the sample.

The label analog is included in the reaction mixture to interact with the potentially interfering substances from the sample in place of the label portion. Accordingly, the effective concentration of the labeled reagent available for binding and detection is substantially less affected by the sample interferences. Of course, the label analog must be selected to be sufficiently similar to the label portion to interact effectively with the interfering substance while being sufficiently dissimilar so as not to significantly provide the detectable response which characterizes the label portion. Normally, a sufficient amount of the label analog can be added to significantly improve the precision of the assay.

Reduction of sample interference effects according to the principles of the present invention can be applied to any specific binding assay wherein the amount or concentration of the labeled reagent in the assay mixture is critical to assay performance and wherein the sample may potentially include substances that would effectively alter the amount or concentration of labeled reagent by interactions, such as binding, with the label portion thereof. The invention is particularly useful in homogeneous assays since such assays are characterized by the formation of assay mixtures which contain both test sample and labeled reagent and therefore provide ample opportunity for sample interfering substances to interact with the labeled reagent. Likewise, heterogeneous assays having protocols wherein sample and labeled reagent are incubated together for a period of time sufficient to adversely affect the assay performance in the absence of the label analog are improved by the present invention. Preferably then, the label analog will be present in the assay at all times that the labeled reagent is incubated with the test sample.

As is described in detail below, particularly in the Examples, the origin of the present invention was the need to reduce or eliminate serum interferences in an apoenzyme reactivation immunoassay system (ARIS), particularly where the analyte needed to be detected at relatively low concentrations in the test sample, e.g., an assay for the cardiac drug digoxin. In the ARIS assay, the reagent system comprises (i) a labeled reagent having a flavin adenine dinucleotide (FAD) label portion coupled to the analyte or a binding analog thereof, (ii) an antibody capable of binding to the analyte and to the FAD-labeled reagent, and (iii) catalytically inactive apoglucose oxidase. The FAD-labeled reagent is capable of combining with the apoglucose oxidase to form catalytically active holoenzyme glucose oxidase. The binding of antibody to the FAD-labeled reagent, however, reduces the ability to combine with apoglucose oxidase. Thus, the proportion of antibody-bound species of the labeled reagent to the antibody-unbound or free-species can be determined in the assay mixture without separation of the two species by measurement of the bulk glucose oxidase activity that results.

In the course of developing an ARIS assay for digoxin a variable serum effect was observed which unacceptably limited the precision of the assay. A variety of potential cures were investigated since the cause of the interferences was not obvious or readily discoverable. Of the many possible mechanisms of interference, one theory suggested that the use of a structural analog of FAD could possibly reduce the sample effect. After some investigation of this theory and many unsuccessful efforts using other possible cures, the use of a flavin structural analog such as flavin mononucleotide (FMN) or riboflavin was found to have a significant positive effect in reducing sample interferences and improving assay precision.

DESCRIPTION OF THE PREFERRED EMBODIMENTS

Figure 1:
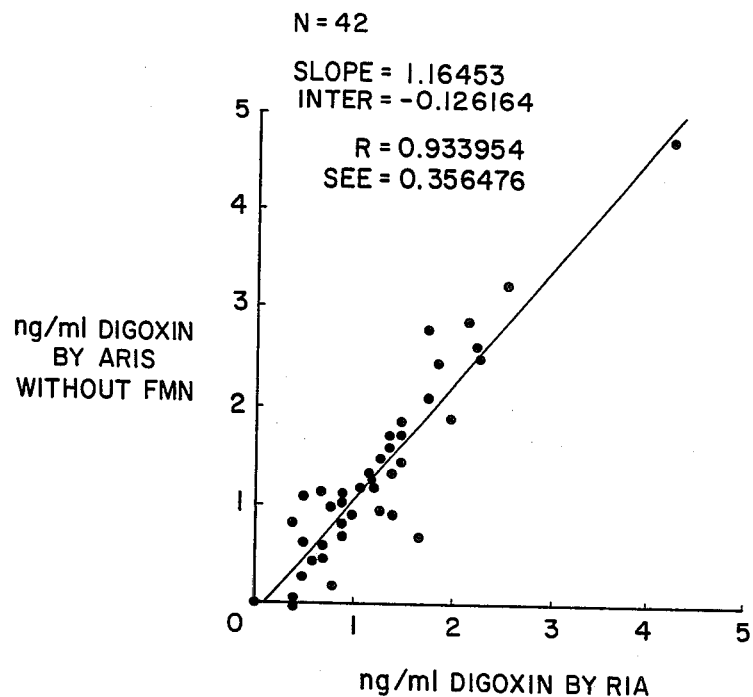
FIGS. 1 and 2 are graphs comparing the correlation of the ARIS digoxin assay to a standard RIA method with (FIG. 2) and without (FIG. 1) the FAD analog in the ARIS assay.

The presence of the label analog in the assay mixture serves to block the interfering interaction that would otherwise take place between the interfering substance from the test sample and the label portion of the labeled reagent. The interaction thus blocked can vary widely depending on the nature of the test sample and the label. Typical interactions would include chemical reactions which would modify or destroy the label, including enzymatic reactions and nonenzymatic reactions, and binding interactions which may be nonspecific, e.g., protein/small molecule hydrophobic binding [such as higher order binding of free fatty acids (n>3) to human serum albumin], nonspecific adsorption to assay vessels (such as thyroxine binding to polystyrene), or specific, e.g., immunochemical, drug or hormone receptor interactions, or transport proteins (such as hemopexin which transports heme or human serum albumin which transports bilirubin to the liver for detoxification).

The incidence of interferences affecting the label will depend on the nature of the test sample as well as the label. Test samples that contain a variety of chemically or enzymatically reactive material and/or binding proteins, such as biological fluids, will of course tend to raise more potential interferences. Likewise, the more similar the label is to substances normally found in the test sample, the more likely interactive substances could be present.

The label analog, as a structural analog, of the label portion of the labeled reagent will have minor or major portions of its chemical structure in common with the label. Clearly it is necessary only that the label analog have that arrangement of atoms in common with the label which is the site of interaction with the interfering substance in the test sample. Thus, the label and label analog can overall be quite different in chemical structure so long as the interactive site is common to both. Oftentimes the label analog will be a close analog or derivative of the label, varying only enough to maintain the label analog substantially inactive in the detection system for measuring the label.

In terms of molecular weight, the label analog can be larger, smaller, or approximately the same as the label. Where the label is relatively small, the label analog could for example be relatively larger. For example, the label analog could be a high molecular weight conjugate of the label itself coupled to a polymeric backbone such that the label portion on the label analog is available for binding or interaction with the interfering substance while inactive because of its size or steric configuration in the detection system for the label. Similarly, the label analog could be relatively smaller where the label is of high molecular weight. For example, the label analog could be a subunit or fragment of the label which includes or substantially comprises the site of interaction on the large label molecule. It will be evident to one skilled in the art that there are a variety of size and molecular structure relationships possible between the label and its analog.

It will be particularly preferred that the label analog be small, i.e., of molecular weight less than about 1500, more commonly less than about 1000. The idea of using a label detector analog to reduce or eliminate serum interference can be extended to any of the existing immunoassay technologies (hetero- or homogeneous). This concept basically separates an immunoassay label into two portions, namely, the analyte or analyte specific portion and a detector portion. As the name (detector analog) implies, this idea deals with reduction of serum interferences that act upon the detection portion of immunoassay labels. Basically, immunoassay detector molecules can be categorized by size into two classes: (1) small molecules (e.g., small molecule fluorescent labels-umbelliferone or fluorescein; prosthetic group labels - FAD) and (2) large molecules (e.g., large molecule fluorescent tags - phycobiliproteins; enzyme labels - glucose oxidase, peroxidase or $\beta$-galactosidase).

Clearly, both types of detector molecules (large or small) are subject to positive and negative serum interferences. For example, if an enzyme label is employed it could be activated or inhibited by allosteric effectors (non-active site), or it could be inhibited by competitive inhibitors; such as, substrate analogs, or it could be destroyed by denaturation, heavy metal poisoning (e.g., $Hg^{+2}$) or proteolytic digestion or finally it could be activated or inhibited by the presence of circulating human antibodies to the enzyme. There is a distinct difference between large molecule detector analog and small molecule detector analog relief of serum interferences. A recent article describing a homogeneous immunoassay for serum ferritin best illustrates this difference (Armeta et al, supra). Basically, this technology is a homogeneous enzyme inhibitor immunoassay that involves the ability of analyte-specific antibody to modulate (inhibit) the enzyme activity of an analyte-$\beta$-galactosidase label toward a macromolecular fluorogenic substrate (i.e., $\beta$-galactosylumbelliferone 3-carboxylic acid coupled to amino dextran). During this study, severe interference was observed with some individual serum specimens. This interference caused inhibition of the analyte(ferritin)-$\beta$-galactosidase activity with the immobilized fluorogenic substrate. Preliminary studies (e.g., dialysis of discrepant serum samples and label activity with inhibitory samples and free fluorogenic substrates) indicated that the inhibitory factor was macromolecular and its mode of action was to sterically prevent the label from interacting with the macromolecular substrate. Subsequent studies (e.g., relief of inhibition by pre-treatment of samples with $\beta$-galactosidase-Sepharose or anti-human IgG) suggested that the inhibitory factor was a human-IgG molecule directed against E. Coli $\beta$-galactosidase. In order to minimize or eliminate this serum interference two approaches were investigated; namely, covalent attachment of human serum albumin to the ferritin-$\beta$-galactosidase conjugate (steric hinderance of interferring antibody binding) or the use of inactive $\beta$-galactosidase (a detector analog). Although both approaches reduced serum interference, the latter was utilized in the final assay format. Clearly, the use of inactive $\beta$-galactosidase to reduce or eliminate serum interference in an immunoassay is representative of a high molecular detector analog approach. However, this differs slightly from a low molecular weight detector analog approach in that inclusion of an excess inactive protein to protect active proteins from inactivation (due to any mechanism) is common practice; whereas, the use of a low molecular weight form of proteins; such as, subunits, fragments or peptides have not been commonly utilized for this purpose. Therefore, the physicochemical properties of the inactive proteins; namely, molecular size conformation, immunoreactivity, endogenous small molecule binding specificities and capacities may affect the efficiency of these molecules for relieving interferences. In fact, if one assumes that the interference is due to a detector enzyme specific human antibody, then inactive intact enzyme may not only function as a way to reduce interference but may also participate as an interferent. For example, if the detector enzyme requires activating antibodies (e.g., mutant $\beta$-galactosidase) or stabilizing antibodies (e.g., apoglucose oxidase at elevated temperatures) for activity, the presence of inactive but intact (immunologically) enzymes as detector analogs could cause serious problems. This probably would not occur if a low molecular weight detector analog; such as, a peptide containing the epitope for the interfering human antibody were utilized.

The present invention is applicable to specific binding assays employing virtually any type of labeling substance. Labels useful in such assays are well known in the art and include enzymatically active groups such as enzyme substrates (see U.S. Pat. No. 4,492,751 and British Pat. No. 1,552,607), coenzymes or cofactors (see U.S Pat. Nos. 4,230,797 and 4,238,565), and enzyme modifiers, particularly inhibitors (see U.S. Pat. No. 4,134,972), as well as enzymes themselves (see. U.S. Pat. Nos. 3,654,090 and 3,81,837); fluorescent molecules (see U.S. Pat. Nos. 3,996,345 and 4,160,016, and J. Exp. Med. 1 22:1029(1965); chromogens; luminescers such as chemiluminescers and bioluminescers (see U.S. Pat. No. 4,380,560); specifically bindable ligands such as biotin or haptens; and so forth. Illustrations of some particular labeling substances and potentially useful label analogs follow.

For example, this approach could be applied to the fluorescence polarization immunoassay (FPIA) technology such as described in U.S. Pat. No. 4,510,251. In order to eliminate assay interference associated with label (analyte analog coupled to fluorescein) nonspecific binding, samples (calibrators, controls and clinical specimens) are pretreated with trichloroacetic acid to precipitate serum proteins. Alternatively, following the present invention, a non-fluorescent fluorescein analog could be included (in excess) in an assay reagent (e.g., antibody reagent) which would saturate the label nonspecific binding sites found on the interfering serum proteins. Such an approach would eliminate the need for sample pretreatment. In addition, fluorescein analogs possessing fluorescent properties that do not interfere (e.g., quench or transfer fluorescence) with those of the analyte-fluorescein label can be employed.

A second example of where the detector analog concept can be applied to relieve serum interferences in an immunoassay is the Apoenzyme Reactivation Immunoassay System (ARIS) as described in U.S. Pat. No. 4,238,565. In this system, analyte and label [analyte covalently attached to flavin adenine dinucleitode (FAD)]compete for a limiting number of antibody binding sites. Antibody bound label is incapable of recombining with apoglucose oxidase (inactive) whereas the free label can reassociate (through its FAD portion)

with the apoenzyme to form active glucose oxidase which can be detected by coupling its activity with horseradish peroxidase and chromogenic substrates. Clearly, if the label concentration in the assay were reduced in a variable manner by individual serum samples, a significant assay interference would exist. Utilizing an analog of the detection portion of the assay label (FAD); such as, flavin mononucleotide (FMN) or riboflavin (Vitamin $B_2$) can eliminate this interference since these molecules in excess would be reduced (e.g., destroyed chemically or enzymatically or bound to serum proteins) instead of the label. An additional requirement of these FAD analogs would be that they can not interfere with label binding to apoglucose oxidase.

Essentially any type of specific binding assay technique in which the addition of label analog reduces sample interferences can be employed. Included are heterogeneous assays wherein the bound- and free-species of the labeled reagent are separated physically and the label measured in one thereof, and especially homogeneous assays wherein the label provides a measurably different response in the two species so that separation is not necessary. The binding interaction forming the basis of the assay can be an immunochemical binding, for immunoassays, a complementary polynucleotide binding, for nucleic acid hybridization assays, or any other mutual binding interaction as are known in the art. The assay protocol can vary widely and can include competitive binding, direct binding, immunometric, sequential saturation, and sandwich protocols. These features of the assay are not critical and are a matter of choice to the worker in the field.

The analyte to be determined can likewise be any substance capable of detection by specific binding assay. Normally the analyte will be a peptide, polypeptide, protein, carbohydrate, glycoprotein, steroid, nucleic acid, or any organic molecule for which a specific binding counterpart exists or can be prepared. Normally, the analyte will, in functional terms, be selected from the group comprising antigens, haptens and antibodies thereto; complementary polynucleotides; and hormones, vitamins, metabolites and drugs, and their binding proteins, receptors, and the like. Further elaboration of analytes can be found in U.S. Pat. No. 4,238,565.

The present invention will now be illustrated, but is not intended to be limited, by the following examples.

EXAMPLE 1

Conception of Possible Solutions to the Problem of Serum Interferences in ARIS Assay As discussed above, the ARIS procedure (Apoenzyme Reactivation Immunoassay System) provides a homogeneous immunoassay employing flavin adenine dinucleotide (FAD) as the labeling substance. The ability of the label reagent (the FAD labeled analyte conjugate) to recombine with catalytically inactive apoglucose oxidase to form active glucose oxidase holoenzyme is inhibited upon binding of the label by analyte specific antibody.

In order to reduce or eliminate a serum interference that was not corrected for by an assay blank, a number of experimental approaches were investigated. A previous normal human serum study suggested the differences between individual serums when assayed using the ARIS procedure were associated with variation in the assay reactions but not the sample blanks. These data indicated that normal human serum variation in the assay was associated with differences in the assay label (i.e., analyte-FAD) concentrations of the reaction since the blanks contain no label and were unaffected. Based on these data the following mechanisms were envisioned: (1) competitive inhibitors of apoglucose oxidase were present in varying amounts in individual serums and prevent reconstitution of label and apoenzyme, (2) large or small molecules present in serum bind or complex with the label molecule rendering it inactive (i.e., preventing it from recombining with the apoenzyme) or (3) large or small molecules present in serum chemically modify or destroy the label rendering it inactive.

If this endogenous serum interference was due to label nonspecific binding, it was conceived to saturate these nonspecific binding sites with structural analogs of the ARIS label. Therefore, two types of label analogs are possible: (1) analogs of the analyte and (2) analogs of the detector molecule (FAD). In both cases, these analogs would have to possess special properties; that is, in the case of an analyte analog, it must relieve the nonspecific label binding (possibly by binding to the interfering substance) without binding tightly to the analyte specific antibody utilized in the immunoassay, whereas in the case of a detector analog it must also relieve the nonspecific binding of label without affecting the detection system of the immunoassay employed. For the ARIS system this means a detector analog cannot interfere with the following steps of the detection system: (1) label/apoenzyme binding (i.e., analog cannot bind tightly to apoenzyme), (2) rate of $H_2O_2$ production (i.e., analog cannot be a positive or negative effector of glucose oxidase or a scavenger of $H_2O_2$, (3) rate of chromophore production (i.e., analog cannot be a positive or negative effector of peroxidase or substrate for peroxidase), or (4) spectral determination of chromophore.

Due to the ready-availability of ARIS label detector analogs; namely, flavin mononucleotide (FMN) and riboflavin (vitamin $B_2$) this hypothesis was investigated first. Two preliminary experiments involved the manual addition of a constant volume (10 μL) of a flavin analog at a variety of concentrations (viz., FMN at 0–1000 μM and riboflavin at 0–1 μM) during the antibody/sample incubation. These experiments were performed on five (riboflavin) and six (FMN) fresh normal serum specimens. A detailed description of the experimental protocol utilized for these studies is outlined below applied to the determination of digoxin.

EXAMPLE 2

ARIS Assay for Digoxin

All data was collected utilizing ARIS on the OP-TIMATE ™ automated fluorometer/photometer (Miles Laboratories, Inc., Elkhart, IN USA) in the absorbance mode with the following reagents and calibrators. Antibody reagent: Per milliliter, 1.6 μL of digoxin specific rabbit antiserum, 240 μL of glucose oxidase specific goat antiserum, 106 μmol sodium phosphate, pH 7.0, 0.15 mmol sodium chloride and 0.2 mg merthiolate. Label reagent: Per milliliter, 34 pmol digoxigenin-FAD, 50 μmol 2-(N-morpholino) ethane sulfonic acid, pH 6.0, 0.1 mg Triton X-100 and 0.2 mg merthiolate. Enzyme reagent: Per milliliter, 7.58 nmol apoglucose oxidase, 0.1 mmol sodium phosphate, pH 7.4, 0.5 mL of glycerol, 10 μmol 4-aminoantipyrene (4-AP) and 0.2 mg merthiolate. Phosphate Glucose buffer: Per liter, 0.217 mol dextrose, 0.475 mol sodium phosphate, pH 6.5 and 0.2 g sodium azide. Dry Buffer blend: Per gram, 16.4 mg peroxidase (specific activity 234 mI.U./mg), 62.4 mg potassium ferrocyanide and 921.2 mg 3,5-dichloro-2-hydroxybenzene sulfonate (DHSA). Composite Reagent: Reconstitute one bottle of dry buffer blend (~800 mg) with one bottle of phosphate glucose buffer (450 mL). Per liter, 0.217 mol of dextrose, 0.375 mol sodium phosphate, pH 6.5, 7.5 I.U. peroxidase, 6.7 mmol DHSA, 318 mmol potassium ferrocyanide and 0.2 g sodium azide. Calibrators: These were prepared from a 50 mg/L digoxin 80% (v/v) ethanolic primary stock solution. A secondary ethanolic stock solution containing 5 mg/L digoxin was prepared by serial dilution. The final working solution was 50 µg/L digoxin in aerosil-treated normal human serum. The working solution was diluted to 0, 0.6, 1.2, 2.4, 3.6 and 5.0 µg/L with aerosil-treated normal human serum.

Assay Procedure: The ARIS digoxin assay was performed at pH 6.5 and 37° C. The assay protocol utilized a sequential saturation format. In the first step, sample (50 µL), antibody reagent (20 µL) and composite reagent (300 µL) are added to an OPTIMATE reaction cup. After a 19-minute incubation period, label reagent (20 µL) and composite reagent (200 µL) are added to the reaction cup. Then 8 seconds later enzyme reagent (20 µL) and composite reagent (400 µL) are dispensed into the reaction cup to initiate the reaction. Following a 17.1 minute reaction time, the reaction mixture (1.01 mL) is aspirated automatically into the OPTIMATE flow cell where its absorbance at 520 nm is measured. In order to correct for endogenous serum interferences (e.g., ascorbic acid) a blank is performed on every sample. The blanking procedure protocol is identical to the assay protocol above except that during the second step no label reagent is added; however, the assay volume is conserved by adding 20 µL of additional composite reagent. The difference in absorbance at 520 nm between the reaction mixture and blank [i.e., $A_{520}$ (reaction) $- A_{520}$ (blank) $= \Delta A_{520}$] for each sample is related to digoxin concentration by means of a standard curve.

The results of the effects of flavin analogs on the performance of the ARIS digoxin assay with normal (non-digoxin)-human serum specimens are summarized in Tables 1 and 2. The apparent digoxin concentrations are calculated assuming a standard curve range of 300 mAs at 520 nm.

TABLE 1

Effect of FMN on the ARIS Digoxin Assay with Normal Human Serums

| Sample | [FMN] µM | Apparent [Digoxin] ng/mL |
|---|---|---|
| 1 | 0 | −1.26 |
|   | 10 | 0.12 |
|   | 1000 | 0.13 |
| 2 | 0 | −1.40 |
|   | 10 | −0.12 |
|   | 1000 | −0.17 |
| 3 | 0 | 0.15 |
|   | 1 | 0 |
|   | 10 | 0.08 |
| 4 | 0 | −0.68 |
|   | 1 | −0.03 |
|   | 10 | 0.19 |
| 5 | 0 | 0.32 |
|   | 1 | 0.23 |
|   | 10 | 0.31 |
| 6 | 0 | −0.42 |
|   | 1 | 0.16 |
|   | 10 | 0.11 |

TABLE 2

Effect of Riboflavin on the ARIS Digoxin Assay with Normal Human Serums

| Sample | [Riboflavin] µM | Apparent [Digoxin] ng/mL |
|---|---|---|
| 1 | 0 | −0.05 |
|   | 1 | 0 |
| 2 | 0 | −1.68 |
|   | 1 | −0.10 |
| 3 | 0 | 0.20 |
|   | 1 | 0.18 |
| 4 | 0 | −1.50 |
|   | 1 | 0.01 |
| 5 | 0 | −0.86 |
|   | 1 | −0.06 |

Table 1 demonstrates the ability of FMN to relieve the normal human serum interference observed with the ARIS digoxin assay. Probably the most striking examples of the FMN effect are samples 1 and 2 which in the absence of the flavin analog exhibited apparent digoxin values <0 mg/mL by >1 ng/mL whereas with the detector analog present at a final concentration of 10 or 1000 µM these serums read approximately 0 ng/mL. Serum samples 3 and 5 were included in this study in order to assess the effect of FMN on non-interfering serum samples. Clearly, 1 and 10 µM FMN did not significantly affect the assay results of these serums. Similar results were obtained when riboflavin was substituted for FMN as the flavin analog. For example, two serum samples (2 and 4) which exhibited severe interference in the ARIS digoxin assay could be corrected for by the inclusion of riboflavin (1 µM final assay concentration) during the sample/antibody incubation.

In addition, the same concentration of riboflavin did not adversely affect non-interfering serum results (e.g., samples 1 and 3). Clearly, the presence of FMN or riboflavin during the sample/antibody incubation step of the ARIS digoxin assay reduced or eliminated the interference observed with normal human serum specimens. Based on these findings it was apparent that one of these compounds would have to be included in either the antibody reagent or composite buffer since only these reagents are present (in both the reaction and blank cups) during the sample/antibody incubation step. In order to ensure that all of the flavin analog was added to the sample in a single step, it was added to the antibody reagent. Since only 20 µL of antibody reagent is added to each cup, a concentrated flavin solution is required; therefore, FMN was the compound of choice due to its superior solubility (relative to riboflavin) in aqueous systems.

Figure 2:
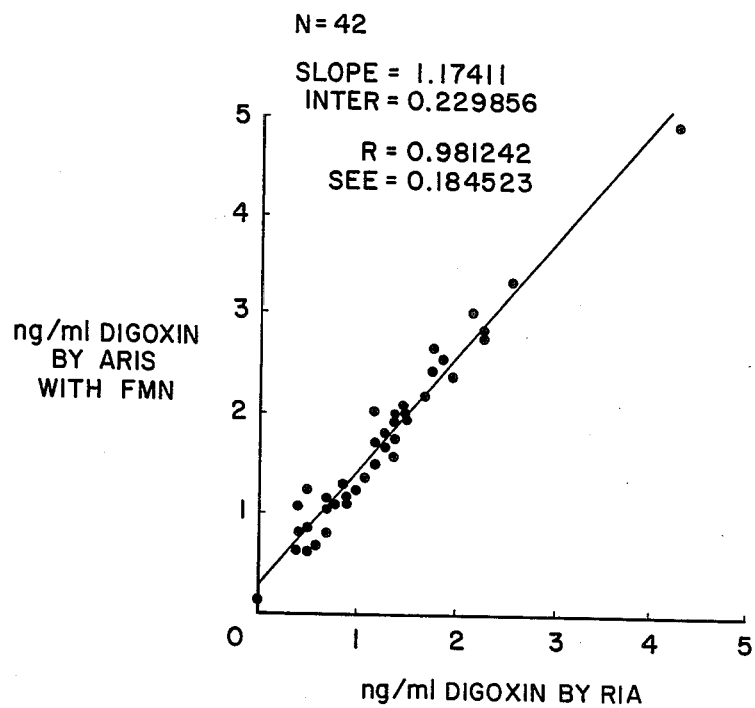

In the following clinical correlation study (n=42), specimens were assayed in duplicate utilizing the ARIS digoxin assay with and without FMN. This was accomplished using antibody reagent with and without 0.5 µmol FMN per milliliter. The data was collected on the OPTIMATE as previously described. The reference assay values were obtained using the Nuclear Medical Laboratories (NML, Irving TX, USA) Digi-Tab radioimmunoassay. The results of this study are shown in FIGS. 1 and 2. These figures show graphically the clinical correlations obtained in the absence (FIG. 1) and presence (FIG. 2) of FMN. Clearly, the most significant feature of these data is the improvement in the standard error of the estimates (S.E.E.; a measure of the degree of scatter) in the presence of FMN [i.e., 0.356 ng/mL (minus FMN) and 0.184 ng/mL (plus FMN)]. In addition, two specimens which read ~0 ng/mL digoxin via ARIS assay (minus FMN) were shown to agree with the reference procedure when FMN was present in the system. The reduction in scatter observed when FMN was included in the ARIS digoxin assay was also evident in the correlation coefficient (r) which increased from 0.934 to 0.981. Based on these data it is clear that inclusion of flavin analogs during the sample/antibody incubation step of the ARIS assay improves its performance.

EXAMPLE 3

ARIS Assay for Human Chorionic Gonadotropin (hCG)

Previous studies involving ARIS assays for low level protein analytes (e.g., IgE and hCG) demonstrated that these procedures also exhibited severe interference with some normal human serums. In order to study the effect of flavin analogs in low level protein ARIS assays, a series of experiments were performed. In all cases the following manual assay protocol was employed. FAD-conjugate was incubated in 2.0 mL of assay mixture containing 10 mM DHSA, 0.1M glucose, 25 μg/mL horseradish peroxidase, 0.1% bovine serum albumin (BSA) in 0.1 M sodium phosphate at pH 7.0 with or without 5% serum and/or 10 μM FMN. After 30 minutes at 37° C., 100 μL of apoglucose oxidase/antiglucose oxidase (3 μM apoenzyme) in 50% glycerol and 4 μM 4-aminoantipyrene was added to initiate the reaction. Following a 30 minute assay incubation step at 37° C. the absorbance was measured at 520 nm.

The first experiment involved the incubation of 5 nM hCG-FAD with three different serum samples; namely, a serum pool exhibiting strong interference and two individual fresh normal human serums. The results are shown in Table 3. Two controls were performed during this experiment: (1) conjugate, no serum, no FMN (maximum activity) and (2) conjugate, no serum, plus FMN (assess FMN effect on maximum activity).

TABLE 3

Effect of FMN on the hCG ARIS assay

| Condition | Corrected ΔA520 | % Activity | |
|---|---|---|---|
| Conjugate | 471 | 100 | |
| Conjugate + FMN | 429 | 91 | 100 |
| Conjugate + Pool | 105 | 22 | |
| Conjugate + Pool + FMN | 412 | 87 | 96 |
| Conjugate + Serum 1 | 89 | 19 | |
| Conjugate + Serum 1 + FMN | 399 | 85 | 93 |
| Conjugate + Serum 2 | 278 | 59 | |
| Conjugate + Serum 2 + FMN | 394 | 84 | 92 |

The results demonstrate that FMN decreases the maximum activity of the conjugate by ~9%. The corrected absorbances in Table 3 are expressed in mA units. All three serum samples in the absence of FMN exhibited a high degree of interference which is expressed as a percentage of the maximum activity observed in the absence and presence of FMN. The inhibition of maximum activity observed with these three samples in the absence of FMN ranged from 51–81%. The same three samples in the presence of FMN exhibited only 4–8% inhibition of maximum activity. Therefore, the presence of a flavin analog (FMN) in the ARIS hCG assay was effective in reducing or eliminating interference due to normal human serums.

EXAMPLE 4

Investigation of the Nature of the ARIS Serum Interference

In order to determine the nature of the ARIS serum interference the following experiment was performed. An inhibitory normal human serum was chromatographed on a Sepharose-Protein A column in order to absorb out the human IgG. Then the IgG was eluted off of the Protein A column yielding an immunoglobulin fraction with a protein concentration of 10.7 mg/mL. Utilizing the hCG-FAD conjugate (5 nM) the serum, absorbed serum (non-Protein A bound fraction; serum minus IgG) and the IgG fraction were assayed in the absence of FMN in order to determine which fraction was inhibitory. Clearly, the data in Table 4 demonstrate that the serum factor responsible for inhibition is associated with the IgG fraction; that is, the intact serum which exhibits ~80% inhibition when fractionated demonstrates inhibition only in the IgG fraction (Protein A absorbed material).

TABLE 4

| Condition | Corrected A520 | % Activity |
|---|---|---|
| Conjugate | 447 | 100 |
| Conjugate + Serum | 89 | 20 |
| Conjugate + Absorbed Serum | 460 | 103 |
| Conjugate + IgG | 79 | 18 |
| Conjugate + IgG + FMN | 423 | 95 |

When the IgG fraction is assayed in the presence of FMN the inhibitory effect of this sample was essentially eliminated (i.e., 82% inhibition minus FMN and 5% inhibition plus FMN). In addition, a concentrate of this IgG fraction (25.6 mg/mL) was shown to inhibit a low molecular weight FAD-conjugate in the absence of FMN. Based on the serum fractionation data (obtained with protein-FAD conjugates) and the proposed mechanism of serum interference, a literature search for flavin-binding proteins in human serum was performed. Two relevant articles were identified: (1) "Myeloma with Xanthoderma due to an IgGλ Monoclonal Anti-Flavin Antibody", Farhangi, M. and Osserman, E. F., N. Engl. J. Med. 294, 177–183 (1976) and (2) "Recent Findings Concerning Mammalian Riboflavin-Binding Proteins", Merrill, A. H., Jr., Shapira, G. and McCormick, D. B., In *Flavins and Flavoproteins*, Massey, V. and Williams, C. H., Eds., Elsevier/North Holland, Inc., New York, N.Y. pp. 508–513 (1982).

The first article describes the presence of a riboflavin-binding monoclonal antibody in the serum of a patient with multiple myeloma. This antibody was shown to contain two types of flavin-binding sites: (1) one irreversible site and (2) one high affinity (reversible) site [Kd=(riboflavin) 0.6 nM]. In addition, this paper describes competitive-binding studies involving flavin analogs and [$^{14}$C]-labeled riboflavin. The results indicated that FMN bound equally well to this antibody as riboflavin but that FAD bound strongly to the antibody but not as tightly as FMN or riboflavin. The concentration of riboflavin-binding IgG in this patient's serum was ~94 mg/mL. Assuming a molecular weight of 150,000 Da for IgG and 2 binding sites per molecule, the ratio of FAD binding sites (due to anti-flavin antibody) to FAD-conjugated label in the assay is ~90,000:1. Under these conditions the sample would compete with anti-analyte antibody for FAD-label binding in the reaction; however, the blank which receives no label would be unaffected thereby causing interference. All of the findings in this paper are consistent with our preliminary data and could explain abherant clinical specimens; however, this data does not explain interference observed with normal (non-disease state) human serums.

The second paper describes the presence of riboflavin-binding proteins in normal human serum. These proteins are believed to be IgG, based on the following data: (1) molecular weight 155,000 Da; 55,000 and 25,000 Da upon reduction, (2) binding properties with Protein A and (3) binding properties associated with rabbit anti-human IgG antisera. The article states that these proteins can reach a concentration of 7 mg/100 mL in plasma. Therefore, the molar ratio of FAD-binding sites (due to riboflavin-binding proteins) to FAD-conjugated label in the assay is ~65:1. Of course this assumes no binding sites are occupied by endogenous riboflavin which is not a realistic assumption. However, variations in the endogenous riboflavin concentration could explain both interand intra-patient differences in serum interferences since the riboflavin concentration would affect the amount of FAD-binding sites available for FAD-label binding. In addition, this type of interference could be reduced or eliminated by addition of excess amounts of riboflavin or FMN. The concentration of FMN in the above ARIS digoxin assay (10 μM) relates to a 220-fold molar excess of FMN to riboflavin-binding protein binding sites. All of our data concerning the serum interference with the ARIS digoxin assay is consistent with the existence of flavin binding proteins in normal human serums.

EXAMPLE 5

Use of FMN in ARIS Assays Including Blanking Procedures

Alternative processes designed to eliminate ARIS label non-specific binding were investigated. These approaches involved: (1) changing the ARIS digoxin blanking procedure and (2) changing the ARIS digoxin assay protocol. Changing the blanking procedure from a low activity to maximum activity in order to reduce or eliminate label non-specific binding involved reagent reformulation. Reformulation was necessary since the low activity blank has digoxin-specific antibody present but no label whereas the maximum activity blank has no digoxin-specific antibody but does have label present. These changes in blanking affected only two assay reagents; namely, antibody reagent and phosphate glucose buffer. The new formulations of these reagents are shown below. Antibody reagent: Per milliliter, 1.6 μL of digoxin specific rabbit antiserum, 10.6 μmol sodium phosphate, pH 7.0, 0.15 mmol sodium chloride and 0.2 mg merthiolate. Phosphate glucose buffer: Per liter, 0.217 mol of dextrose, 0.375 mol sodium phosphate, pH 6.5, 8.0 mL of goat antiserum to glucose oxidase and 0.2 g sodium azide. All other assay reagents were identical in composition to those described previously. In addition, the sequential assay protocol timing described earlier was utilized for both blanking procedures; however, reagent dispensing changes were required for the high blank. That is, in the first step of the assay only reaction cups receive 20 μL of AR whereas the blank cups receive only buffer and sample (no antibody reagent). The only other change in the dispense code was the addition of labeled reagent (20 μL) to both the reaction and blank cups.

Utilizing this modified OPTIMATE digoxin assay software, the effectiveness of the maximum activity blank (to reduce or eliminate normal serum interference) was compared to that of the low activity blank. In this study, sixteen samples (plasmas and serums) were assayed in singlicate along with a 0 ng/mL digoxin calibrator utilizing both blank procedures. The results of this study are shown in Table 5. The data is expressed as the difference in mAs between the 0 calibrator and the individual serum or plasma.

TABLE 5

A comparison of assay results obtained with fresh specimens utilizing both the 3-reagent low activity blank and 3-reagent maximum activity blank.

| Sample | Δ "0" Cal low blank mA | Δ "0" Cal high blank − FMN mA | Δ "0" Cal high blank + FMN mA |
|---|---|---|---|
| 1 | −223.3 | +19.1 | +20.3 |
| 1(P) | −177.9 | +17.0 | +14.2 |
| 2 | −220.5 | −13.7 | +14.6 |
| 2(P) | −72.5 | +26.3 | +46.9 |
| 3 | −246.5 | −6.9 | +20.1 |
| 3(P) | −86.9 | +35.8 | +49.9 |
| 4 | −336.9 | −63.7 | −28.8 |
| 5 | −107.4 | +55.0 | +51.1 |
| 5(P) | −113.4 | +47.2 | +39.3 |
| 6 | −109.2 | +5.1 | +32.8 |
| 6(P) | −102.1 | +10.2 | +34.8 |
| 7 | −194.6 | +11.3 | +43.2 |
| 8 | −232.9 | +15.9 | +60.4 |
| 8(P) | −123.4 | +59.1 | — |
| 9 | −170.0 | +43.4 | +52.2 |
| 9(P) | −86.9 | +77.7 | — |
| Total Range | 264.4 | 141.4 | 89.2 |
| x̄ | −158.9 | +23.0 | +32.2 |
| S.D. | 74.1 | 33.4 | 23.0 |
| n | 16 | 16 | 14 |

(P) - plasma (EDTA)

Column 1 shows the results obtained using the low activity blank in the absence of FMN. All of the samples tested read below the 0 calibrator ranging from −72 to −337 mAs which assuming an assay range of 300 mAs translates into samples having negative apparent digoxin values ranging from 1.2 to 5.6 ng/mL. When the same samples were assayed utilizing the maximum activity blank in the absence of FMN the total range in mAs was cut in half (i.e., 264,4 mAs to 141.4 mAs) and not all samples were on the same side of the 0 calibrator (i.e., samples ranged from −63.7 mAs to +77.0 mAs or apparent digoxin concentrations of +1.06 ng/mL to −1.28 ng/mL; see column 2 Table 5). Please note that negative absorbance differences in the maximum activity blank represent positive digoxin values and vice versa. Clearly the maximum activity blanking procedure is superior to the low activity blanking for reducing interference due to normal human serums; however, the total range for normal serums was unacceptable. In order to further reduce the observed serum interference the same samples were assayed utilizing the maximum activity blank in the presence of 10 μM FMN which was introduced via the composite buffer. The results are shown in column 3 of Table 5. These data demonstrate that the presence of FMN in the assay reduced the total range of these samples by ~40% (i.e., 141.4 mAs to 89.2 mAs) and with the exception of one sample all samples read above the zero calibrator (or negative digoxin). The samples ranged from +0.48 ng/mL to −1.01 ng/mL in apparent digoxin concentration; however, this range can be cut in half by elimination of the one negative sample. In any event, FMN was again effective in reducing normal human serum interference in the ARIS digoxin assay.

The present has been particularly described and exemplified above. Obviously, many other variations and modifications of the invention may be made without departing from the spirit and scope hereof.

What is claimed is:

1. In a homogeneous apoenzyme reactivation immunoassay method for determining an analyte in a test sample suspected to contain a potentially interfering binding substance, wherein the test sample is combined with a reagent system that includes (i) a labeled reagent comprising a flavin adenine dinucleotide (FAD) label portion and a specific binding portion comprising the analyte or a binding analog thereof, (ii) an antibody capable of binding the analyte, and (iii) apoglucose oxidase, thereby forming a reaction mixture comprising an antibody bound-species and a free-species of the FAD-labeled reagent, the ability of the FAD-label portion of the labeled reagent to combine with the apoglucose oxidase to produce the catalytically active holoenzyme glucose oxidase being measurably different when the FAD-labeled reagent is in said bound-species compared to when in said free-species, said potentially interfering binding substance being capable of binding with the FAD-labeled portion of the labeled reagent; and wherein the glucose oxidase activity in the reaction mixture is measured and related to the amount of analyte in the test sample;

the improvement which comprises adding to the reaction mixture a flavin structural analog of FAD which does not significantly combine with apoglucose oxidase to produce active glucose oxidase but which binds with the potentially interfering FAD-binding substance.

2. The method of claim 1 wherein the flavin structural analog is flavin mononucleotide (FMN).

3. The method of claim 2 wherein FMN is present in the final reaction mixture at a concentration of at least about 10 $\mu$M.

4. The method of claim 1 wherein the flavin structural analog is riboflavin.

5. The method of claim 4 wherein riboflavin is present in the final reaction mixture at a concentration of at least about 1 $\mu$M.

6. The method of claim 1 wherein the test sample is a biological fluid and the analyte is a hapten or antigen.

7. The method of claim 6 wherein the analyte is digoxin and the biological fluid is blood serum or plasma.

8. In a homogeneous apoenzyme reactivation immunoassay reagent system for determining an analyte in a test sample suspected to contain a potentially interfering binding substance, comprising (i) a labeled reagent having a flavin adenine dinucleotide (FAD) label portion and a specific binding portion comprising the analyte or a binding analog thereof, (ii) an antibody capable of binding the analyte, and (iii) apoglucose oxidase, the ability of the FAD-label portion of the labeled reagent to combine with the apoglucose oxidase to produce the catalytically active holoenzyme glucose oxidase being measurably different when the FAD-labeled reagent is bound by the antibody compared to when not so bound, said potentially interfering binding substance being capable of binding with the FAD-label portion of the labeled reagent;

the improvement which comprises a flavin structural analog of FAD which does not significantly combine with apoglucose oxidase to produce active glucose oxidase but which binds with the potentially interfering FAD-binding substance.

9. The reagent system of claim 8 wherein the flavin structural analog is flavin mononucleotide (FMN).

10. The reagent system of claim 8 wherein the flavin structural analog is riboflavin.

11. The reagent system of claim 8 wherein the test sample is a biological fluid and the analyte is a hapten or antigen.

12. The reagent system of claim 11 wherein the analyte is digoxin and the biological fluid is blood serum or plasma.

* * * * *